United States Patent
Van De Haar et al.

(10) Patent No.: US 7,660,450 B2
(45) Date of Patent: Feb. 9, 2010

(54) IMAGING SYSTEM, AN X-RAY IMAGING APPARATUS, A METHOD AND A COMPUTER PROGRAM ARRANGED FOR REDUCING AN ARTIFACT IN A THREE-DIMENSIONAL RECONSTRUCTED VOLUME

(75) Inventors: Peter George Van De Haar, Eindhoven (NL); Jan Timmer, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 529 days.

(21) Appl. No.: 10/563,921

(22) PCT Filed: Jul. 6, 2004

(86) PCT No.: PCT/IB2004/051135

§ 371 (c)(1),
(2), (4) Date: Jan. 9, 2006

(87) PCT Pub. No.: WO2005/006257

PCT Pub. Date: Jan. 20, 2005

(65) Prior Publication Data

US 2006/0159363 A1    Jul. 20, 2006

(30) Foreign Application Priority Data

Jul. 10, 2003    (EP)    .................................. 03102091

(51) Int. Cl.
*G06K 9/00* (2006.01)
(52) U.S. Cl. .................................... 382/131
(58) Field of Classification Search ......... 382/128–132, 382/205, 298, 299, 300; 378/98.7, 62, 98.3, 378/21, 19, 98.8, 14, 16, 65; 364/413.13, 364/413.23, 413.14, 413.18, 413.19, 413.15, 364/413.26; 128/653.2, 653.1, 920; 250/204, 250/205

See application file for complete search history.

(56) References Cited

U.S. PATENT DOCUMENTS

| 5,434,902 | A | * | 7/1995 | Bruijns | ...................... 378/98.7 |
| 5,692,507 | A | | 12/1997 | Seppi et al. | |
| 5,748,768 | A | * | 5/1998 | Sivers et al. | ................ 382/130 |

FOREIGN PATENT DOCUMENTS

EP    0 479 618 A2    4/1992

(Continued)

OTHER PUBLICATIONS

"Image intensifier distortion correction" Dev. P. Chakraborty, med. phys. 14(2), Mar./Apr. 1987, pp. 249-252.

(Continued)

*Primary Examiner*—Samir A. Ahmed
*Assistant Examiner*—Atiba O Fitzpatrick (57) ABSTRACT

An imaging system including an artifact reducer arranged to correct for a ring-shaped artifact in a three-dimensional reconstructed volume. The artifact reducer includes a first stage correction arranged to eliminate structured noise of an output screen of an image intensifier of an X-ray imaging apparatus using a first corrective image. A raw image of a patient is first processed with the first corrective image. The gain-corrected images are forwarded to an image deformation correction where a suitable unwarping function performed. The gain-corrected unwarped images are then made available to a second stage gain correction where a second corrective image is applied resulting in a final set of images with a substantially reduced ring-shaped artifact. The final set of images is made available to an image reconstructor arranged for further processing of the final set of images, the result thereof being visualized on a computer monitor for inspection purposes.

10 Claims, 7 Drawing Sheets

FOREIGN PATENT DOCUMENTS

| | | |
|---|---|---|
| EP | 0479618 A2 | 4/1992 |
| EP | 0 562 657 A2 | 9/1993 |
| EP | 0562657 A2 | 9/1993 |

OTHER PUBLICATIONS

John M. Boone, et al: Analysis and Correction of Imperfections in the Image Intensifier_TV_Digitizer Imaging Chain, vol. 18, No. 2, Mar. 1991, pp. 236-242, XP002327382.

R. Fahrig, et al: Three-Dimesional Computed Tomographic Reconstruction Using a C-arm Mounted XR11, Correction of Image Intensifier Distortion, vol. 24, No. 7, Jul. 1997, p. 1097, XP012010253.

X. Wang, et al: Accurate and Efficient Image Intensifier Distortion Correction Algorithm for Volume Tomographic Angiography, vol. 37, No. 3, Mar. 1998, pp. 977-983, XP000771077.

\* cited by examiner

IMAGING SYSTEM, AN X-RAY IMAGING APPARATUS, A METHOD AND A COMPUTER PROGRAM ARRANGED FOR REDUCING AN ARTIFACT IN A THREE-DIMENSIONAL RECONSTRUCTED VOLUME

The invention relates to an imaging system arranged to reduce an artifact in a three-dimensional reconstructed volume comprising a plurality of planar images.

The invention further relates to an X-ray imaging apparatus comprising an imaging system arranged to reduce an artifact in a three-dimensional reconstructed volume.

The invention still further relates to a method for reducing an artifact in a three-dimensional reconstructed volume comprising a plurality of planar images.

The invention still further relates to a computer program arranged to carry-out the steps of the above method.

An embodiment of an imaging system arranged to reduce an artifact in an image is known from EP 0 562 657 A2. The known imaging system is used in the field of X-ray diagnostics, where a patient to be examined is positioned between an X-ray source and an X-ray detector arranged to substantially absorb transmitted through the patient X-rays. The X-ray detector comprises an image intensifier arranged to amplify a measured signal. In order to obtain an angulated projection, the X-ray source and the X-ray detector together with the image intensifier are rotated about a rotational axis. The known imaging system is arranged to reduce the image artifact occurring at the edges of the image, known as vignetting, said artifact being caused by a local variation in a gain factor for pixels in an acquisition system. In the known imaging system compensating for vignetting is achieved by multiplying pixel-values of the vignetted image by a gain characteristic yielding from a calibration measurement to obtain an unperturbed image. The gain characteristic is obtained from an image of a calibration object with a known homogeneous brightness distribution.

It is a disadvantage of the known imaging system that a residual image artifact persists in the image corrected for vignetting. In particular, rings appear in slices reconstructed from a three-dimensional data, said slices being spatially oriented perpendicular to the rotational axis around which the image intensifier is rotated during a data acquisition for purposes of the three-dimensional reconstruction. This ring-shaped artifact is caused by a difference in a local response of the image intensifier of the imaging system of the X-ray apparatus.

It is an object of the invention to provide the imaging system where the ring-shaped artifact is substantially reduced.

The imaging system according to the invention comprises image artifact reduction means arranged to subsequently process said planar images with a first corrective image for eliminating a first source of structured noise in said images and a second corrective image for eliminating a second source of structured noise in said images.

The technical measure of the invention is based on the insight that gain differences for the image intensifier are mainly caused by inhomogeneities in the input and output screens of the image intensifier. Such response differences are further referred to as structured noise. The image intensifier suffers from image deformation due to pincushion distortion and due to external magnetic fields, this deformation being dependent on the orientation of the image intensifier. This deformation is referred to as warping. A warped image can be corrected in order to remove warping, said correction being carried out by means of an application of a per se known unwarping function; this being referred to as unwarping. During a three-dimensional scan, the relation between an element on a projection screen, for example a CCD camera of the image intensifier, and a path of an associated X-ray changes due to orientation-dependent image deformation. In order to substantially reduce the image artifact caused by local gain differences in both the input and output screens of the image intensifier a double-stage calibration is performed, by means of the first corrective image and the second corrective image, which independently account for structured noise of the input screen and the output screen of the image intensifier.

In an embodiment of the imaging system according to the invention, the first corrective image comprises a first gain correction data, the second corrective image comprises a second gain correction data.

It is advantageous to use gain correction data for constructing the respective corrective images as the structured noise of the input screen and the output screen of the image intensifier is reflected in local gain differences of respective screens. The first corrective image accounts for the structured noise at the output screen of the image intensifier and the second corrective image accounts for the structured noise at the input screen of the image intensifier. The sources of the structured noise together with corresponding suitable corrective images will be explained in detail with reference to FIGS. 3.

In a further embodiment of the imaging system the first gain correction data comprises a result of an averaging of a plurality of raw images of a gain calibration scan; the second gain correction data comprises a result of an averaging of a plurality of raw images of the gain calibration scan after them being processed by means of the first corrective image and an unwarping function. It is found to be advantageous to construct the first gain correction data from the raw images of the gain calibration scan, which is acquired prior to acquisition of, for example, a patient data scan. The first gain correction is applied to the raw images of the gain calibration scan yielding a set of gain-corrected images of the gain calibration scan, where the high frequency part of the structured noise of the input screen is removed. These images are then processed with a suitable unwarping function after which these images are averaged yielding the second gain correction data corresponding to the structured noise of the input screen of the image intensifier. This embodiment is advantageous as it presents a simple possibility to carry-out a double-stage gain correction correcting for the structured noise of the input and the output screens of the image intensifier separately.

A method for reducing an artifact in a three-dimensional reconstructed volume comprising a plurality of planar images, according to the invention comprises the steps of:

processing the image using a first corrective image to eliminate a first source of structured noise in the image yielding a first-stage corrected image;

processing the first-stage corrected image with a second corrective image to eliminate a second source of structured noise in the image.

These and other aspects of the invention will be discussed with reference to figures.

Figure 1A:
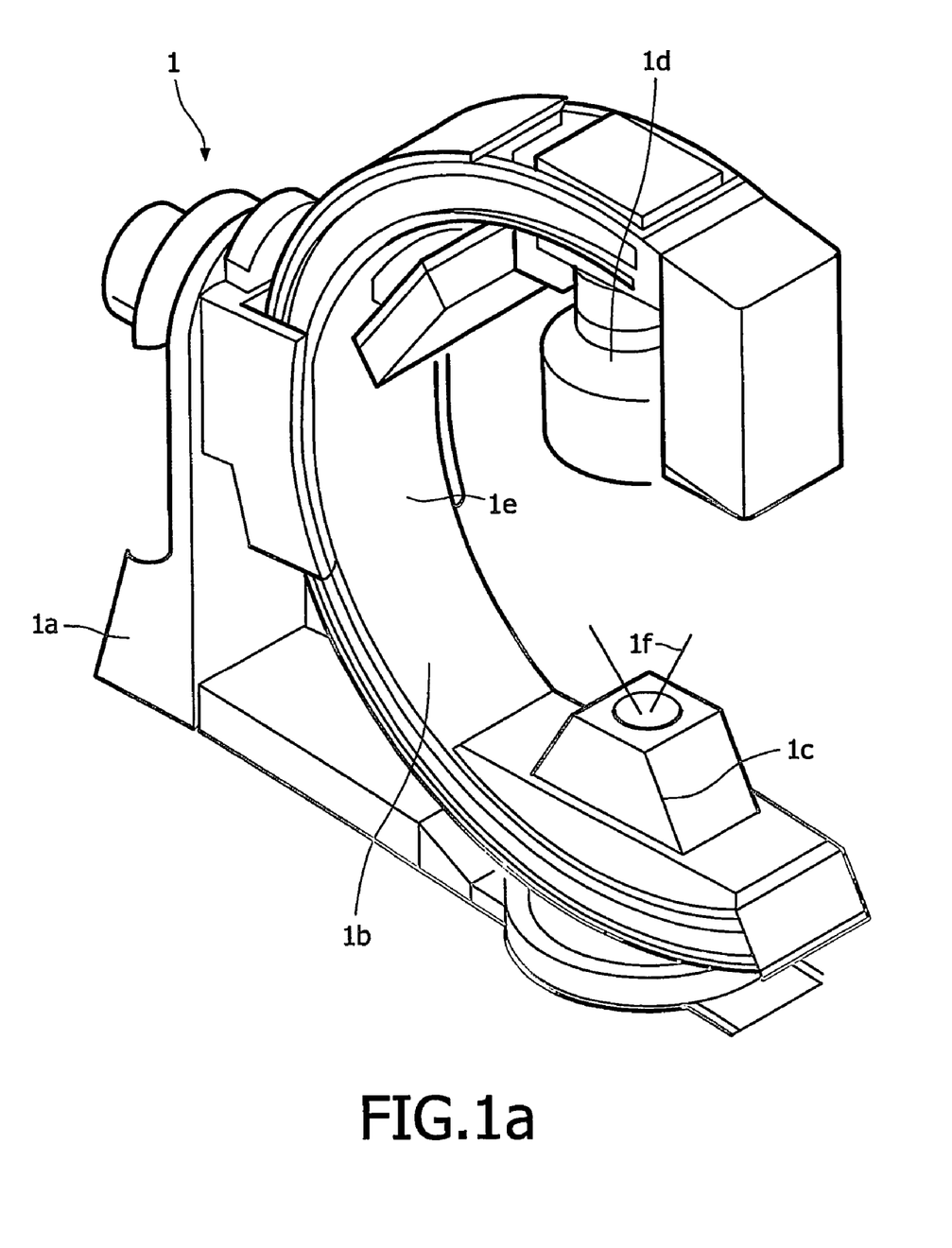
FIG. 1a shows a schematic view of an X-ray imaging apparatus as known in the art.

FIG. 1a shows a schematic view of an embodiment of an X-ray imaging apparatus as is known in the art. The X-ray apparatus 1 comprises a C-arm 1b on which an X-ray source 1c and the X-ray imaging system 1d are mounted. The C-arm 1b is rotatably arranged on a stand 1a. During an acquisition of a three-dimensional scan, the C-arm 1b is rotated around it's rotational axis 1e. The X-rays emanating from the X-ray source 1c are intercepted by the patient (not shown), who is located in an imaging volume between the X-ray source 1c and the X-ray detector 1d. The X-rays 1f emanating from the X-ray source, which are subsequently transmitted through the patient are absorbed by the X-ray imaging system 1d, which is discussed in detail with reference to FIG. 1b.

Figure 1B:
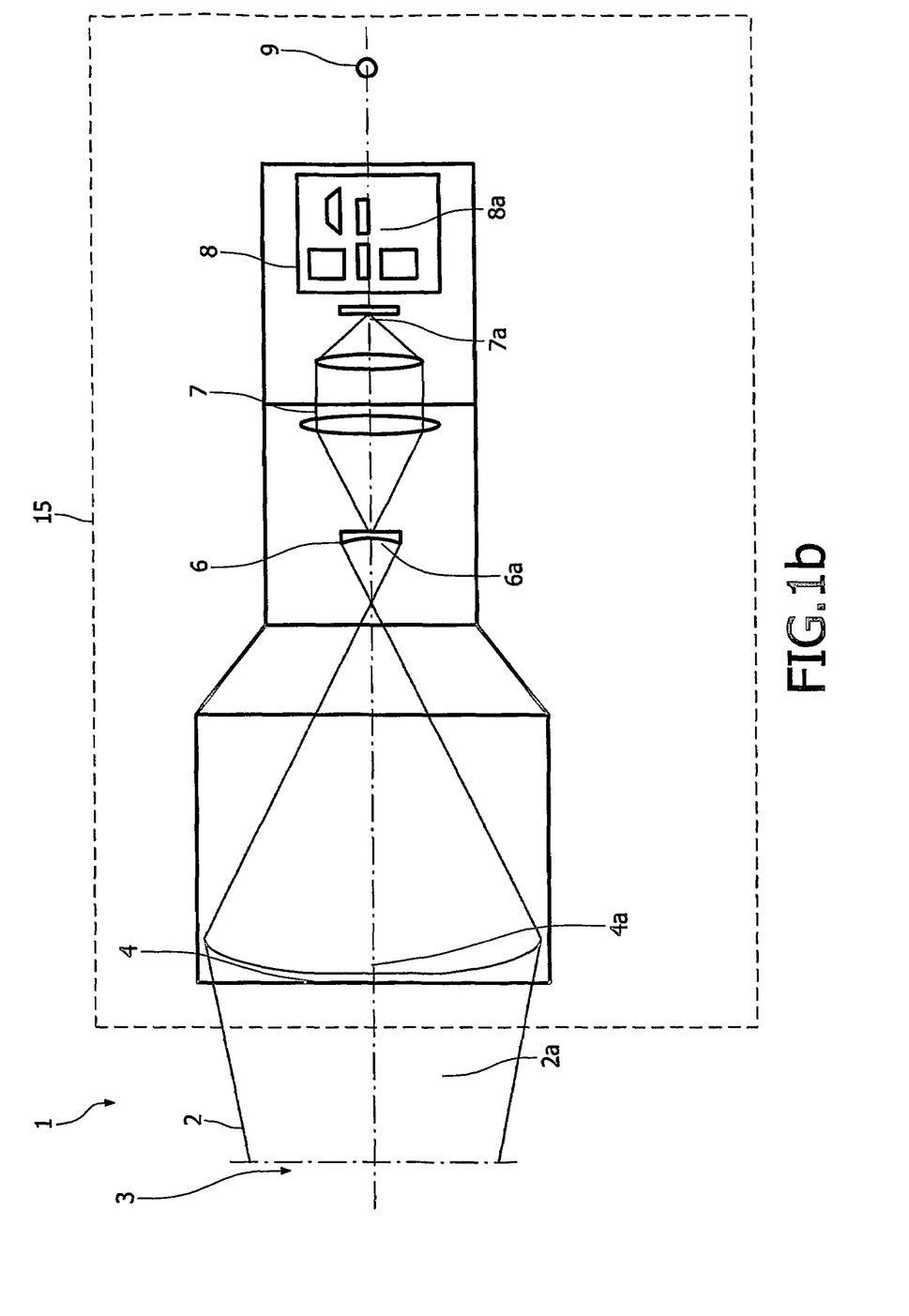
FIG. 1b shows a schematic view of an embodiment of an imaging system of the image intensifier as is used in the X-ray apparatus known in the art.

FIG. 1b shows a schematic view of an embodiment of an imaging system 15 of the image intensifier as is used in X-ray systems known in the art. For medical diagnostics purposes it is conventional to examine a patient in question by means of X-rays. For this purpose the patient 3 is located in an examination space (not shown) of the X-ray apparatus 1 and a set of images with different projection angles is acquired for purposes of a three-dimensional reconstruction. The transmitted X-rays 2 intercept the input screen of the image intensifier 4. The electronic signal is amplified in the image intensifier and is made available to the optics 7 at the output screen 6 of the image intensifier. The light beam is converged at an input of a suitable projection means 8, for example a CCD camera or a CMOS-detector. An output signal from the CCD camera 8 is made available for further processing at the output 9. There are several sources of noise in the X-ray system. First, the X-ray beam 2 comprises an X-ray noise 2a, which is mainly caused by a quantum noise of the X-ray source and contribution of a scatter radiation. The image intensifier has two main sources of noise: a structured noise 4a of the input screen and a structured noise 6a of the output screen of the image intensifier. The optics 7 contributes to the overall noise by its structure noise and a shot noise 7a. Additionally the CCD camera 8 has a readout noise component and an acquisition noise component. It is a common practice to calibrate the CCD camera for gain and offset, therefore the remaining main noise components in the output signal at output 9 comprise the structured noise at the input and output screens of the image intensifier. The contribution of these noise sources to the artifact in a three-dimensional reconstructed volume is shown in detail with reference to FIGS. 2a and 2b.

Figure 2A:
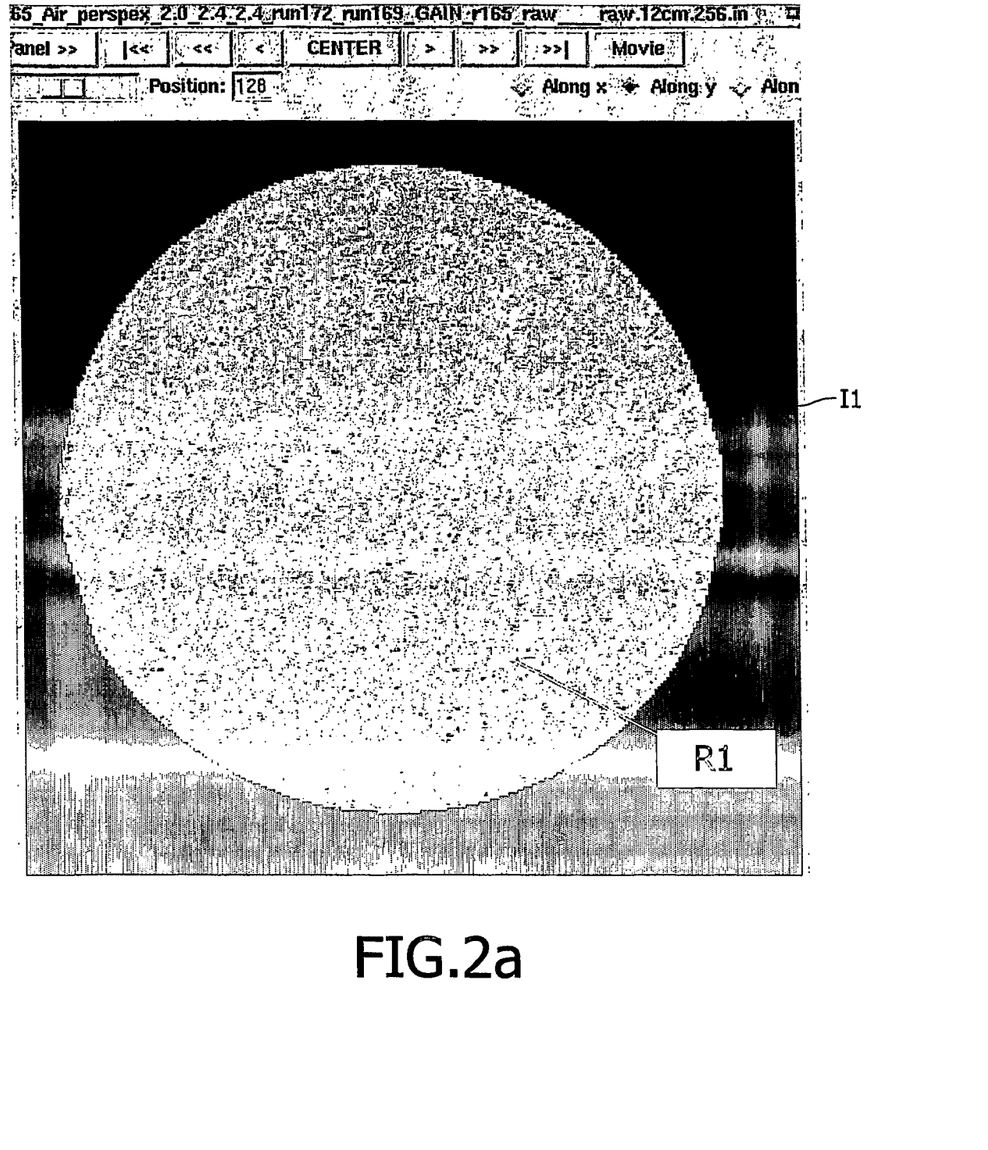
FIG. 2a shows an image artifact in a slice perpendicular to the rotational axis of the X-ray system of FIG. 1a post first gain correction as known in the art.

FIG. 2a shows an image artifact post a per se known gain correction for a slice I1 corresponding to a plane perpendicular to the rotational axis 1e of the image intensifier as is set forth with reference to FIG. 1a. Most commonly, in order to compensate for a gain variation of the output screen of the image intensifier a first corrective image is constructed through averaging a set of raw images, said images preferably being acquired using a homogeneous test phantom. Alternatively, an in-air scan can be acquired for this purpose. An example of a suitable method for an image correction is given by:

$$Im_{gain,single\,stage\,with\,raw\,images}(i, j, n) = Im_{raw}(i, j, n) \frac{\frac{1}{N^2}\sum_{i,j} gain_{raw}(i, j)}{gain_{raw}(i, j)},$$

where $Im_{gain,\,single stage with\,raw\,images}$ is a resulting gain-corrected image of an object under investigation, for example a patient;

$Im_{raw}$ is an original non-processed raw image of the object to be reconstructed, of a three-dimensional scan consisting of M images ($1 \leq n \leq M$);

$gain_{raw}(i,j)$ is a gain value for a pixel (i,j), ($1 \leq i,j \leq N$), for a gain correction image.

From FIG. 2a it follows that using a single gain correction for reduction of the image artifact results in residual rings R1, visible in the slice I1. In spite of the fact that the intensity of this ring-shaped artifact is reduced with respect to the original non-processed image, it is still visible in the resulting gain-corrected image.

Figure 2B:
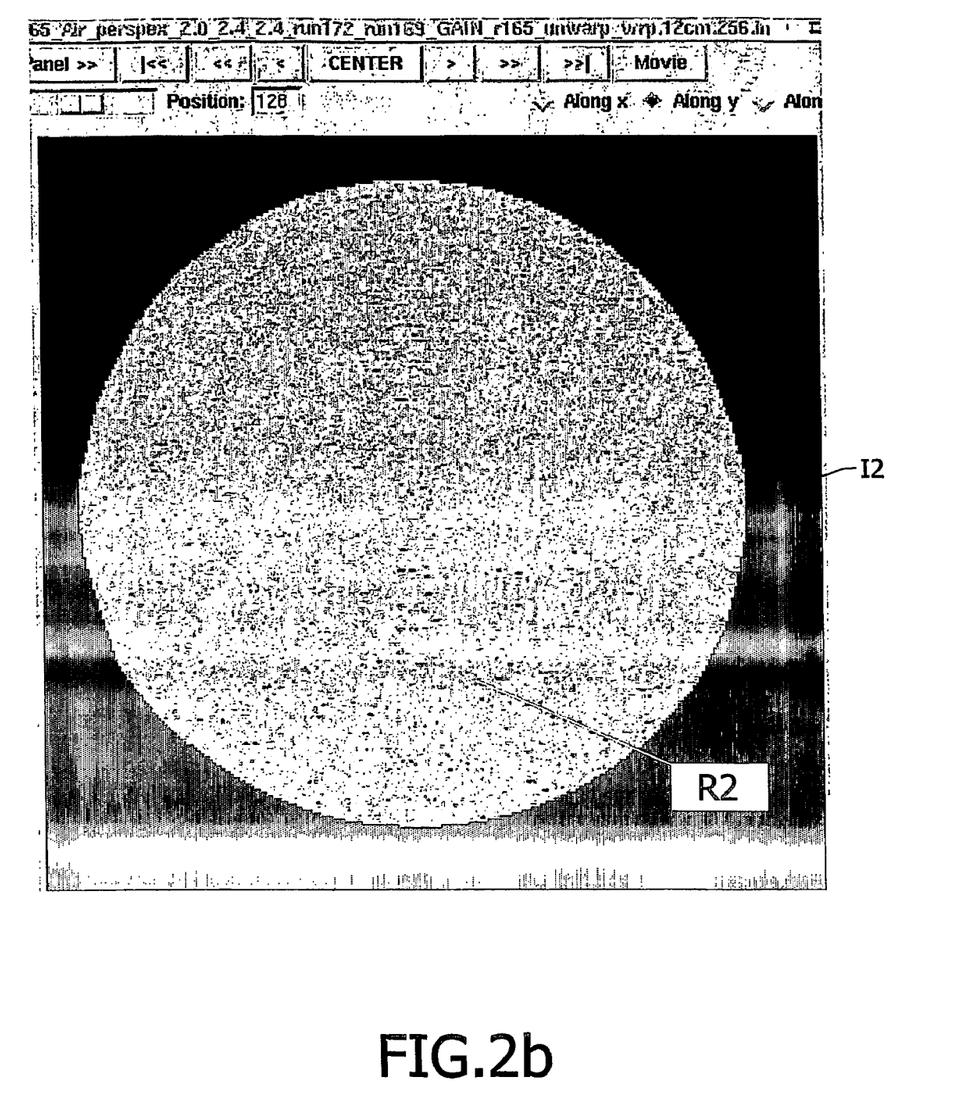
FIG. 2b shows an image artifact in a slice perpendicular to the rotational axis of the X-ray system of FIG. 1a post second gain correction as known in the art.

Another known approach of a single gain correction is to gain correct at the level of unwarped images. FIG. 2b shows an image artifact post first gain correction as known in the art in a slice I2 corresponding to a plane perpendicular to the rotational axis 1e of the image intensifier as is set forth with reference to FIG. 1a. This gain correction is carried out with a single gain image, this gain image being generated through averaging raw images of the gain calibration scan which are unwarped. The unwarping operation results in eliminating the image artifact due to the pincushion and magnetic deformation of the image. Suitable functions to carry out the unwarping operation are known per se in the art. Gain correction of unwarped images is given by:

$$Im_{gain,single\,stage\,with\,raw\,images}(i, j, n) = Im_{unwarped}(i, j, n) \frac{\frac{1}{N^2}\sum_{i,j} gain_{unwarped}(i, j)}{gain_{unwarped}(i, j)},$$

where $Im_{gain,\,singlestagewith\,unwarpedimages}(i,j,n)$ is a value of a pixel (i,j) of a gain-corrected image;

$Im_{unwarped}(i,j,n)$ is an unwarped image, of a three-dimensional scan consisting of M images ($1 \leq n \leq M$);

$gain_{unwarped}(i,j)$ is a gain image constructed for unwarped raw images.

From FIG. 2b it follows that after a single gain correction based on unwarped images the ring-shaped artifacts R2 remain in the reconstructed slice I2.

Figure 3:
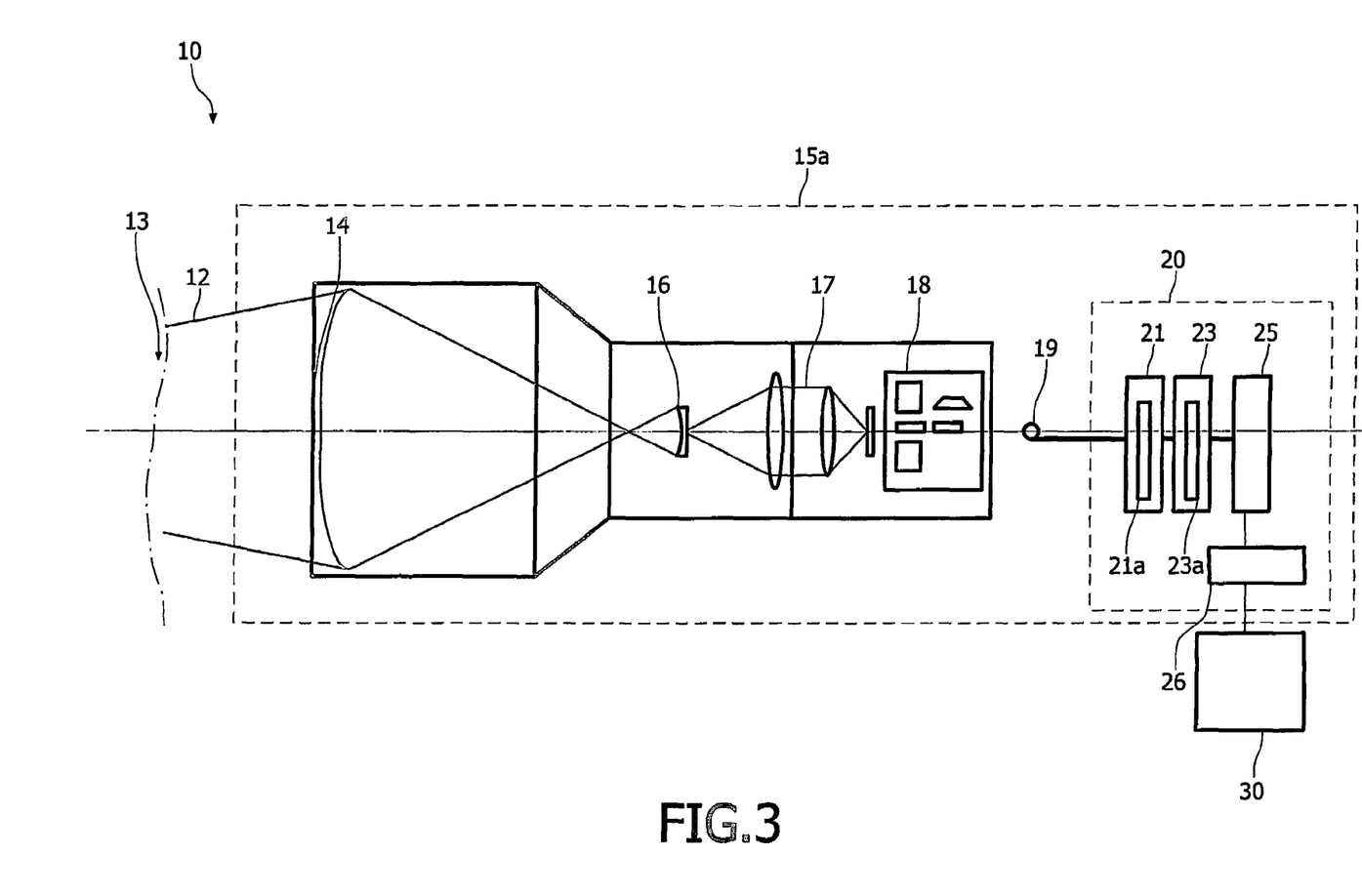
FIG. 3 shows a schematic view of a block diagram of an embodiment of the imaging system according to the invention.

FIG. 3 shows a schematic view of a block diagram of an embodiment of an X-ray examination apparatus comprising the imaging system according to the invention. The X-ray examination apparatus 10 comprises an imaging system 15a arranged with the image artifact reduction means 20 in accordance with the invention. An X-ray beam 12 emanating from an X-ray source (not shown) is transmitted though an object 13 under investigation, most commonly a patient. The X-rays are attenuated by the patient and the attenuated radiation 12 is collected by the input screen 14 of the image intensifier. An X-ray image collected on the input screen of the image intensifier is converted into a visible image on the output screen 16 of said image intensifier. By means of an optical arrangement 17 said visible image is imaged onto an imaging means 18, preferably a CCD camera, whereby the visible image is converted into an electrical analog video signal 19. According to the invention the X-ray apparatus comprises the artifact reduction means 20, said means being arranged to subsequently process the image using a first function for eliminating a first structured noise in the image and a second function for eliminating a second structured noise in the image.

Preferably, to account for the structured noise originating from the output screen of the image intensifier, a first corrective image is constructed through averaging a set of raw images acquired during a three-dimensional gain calibration scan. In order to enable an accurate double stage gain correction for the three-dimensional scan of, for example a patient, the geometry of the three-dimensional scans of the calibration object and the patient has to be substantially the same. The resulting first gain correction data for raw images is given by:

$$gain_{raw}(i, j) = \frac{1}{N}\sum_{i=1}^{N} gain_{raw}(i, j, n),$$

where $gain_{raw}(i,j,n)$ is the series of raw gain images of the gain calibration scan acquired during a three-dimensional scan;

$gain_{raw}(i,j,)$ is the first gain correction data constructed for a set of N gain calibration raw images comprising a i×j number of pixels.

Thus, this operation involves averaging of a set of raw images. Raw image pixels have a one-to-one relation with corresponding elements of the CCD camera, independent of the image number. The elements have a fixed relation with spots on the output screen of the image intensifier, independent of the orientation of the image intensifier. However, due to pincushion deformation, a certain CCD pixel does not have a fixed relation with a spot on the input screen of the image intensifier. Therefore, high frequency structured noise of the input screen is averaged out when constructing $gain_{raw}(i,j)$. So $gain_{raw}(ij)$ describes gain effects of the output screen of the image intensifier, the influence of the input screen being averaged out.

A further method for suppressing the high-frequency part of the structured noise of the input screen is to defocus the image intensifier. It may occur that a projection of the output screen of the CCD camera moves slightly during an acquisition of a three-dimensional scan, it being caused by inertial and gravitational forces which deform the camera assembly; such a movement can be calibrated through analyzing the drift of the structured noise, as observed with the CCD during the gain calibration scan. An example of a suitable drift calibration comprises a parameterization of the movement of the projection of the output screen onto the CCD camera in terms of a x-pixel shift, a y-pixel shift and a rotation of image n of the scan with respect to the image 1 of the scan. This parameterization is then accounted for during a construction of the first gain correction data and is applied to the raw images of the patient scan.

In order to account for the structured noise of the input screen a second corrective image for a set of unwarped images of the gain calibration scan is constructed. The corresponding gain function is given by:

$$gain_{unwarped}(i, j,) = \frac{1}{N}\sum_{i=1}^{N} gain_{unwarped}(i, j, n),$$

where
$gain_{unwarped}(i,j,n)$ is the series of gain images of the gain calibration scan acquired during a three-dimensional scan, said images being corrected with the first corrective image $gain_{raw}(i,j,)$ and subsequently unwarped.

Unwarped image pixels have a fixed relation with a position on the pincushion grid used for a warp calibration, which is used for purposes of unwarping. Therefore, unwarped image pixels have a substantially fixed relation with spots on the input screen of the image intensifier, independent of its orientation. Due to the magnetic image deformation, a certain unwarped image pixel does not have a fixed relation with a spot on the output screen of the image intensifier. Therefore, the structured noise of the output screen is averaged out when constructing $gain_{unwarped}(i,j)$. So, $gain_{unwarped}(i,j)$ describes gain effects of the input screen of the image intensifier, not of the output screen. The effect of the warping is used to separate the structured noise of the input screen and the output screen of the image intensifier.

In order to carry-out a double-stage gain correction of the images of, for example a patient scan, the first corrective image $gain_{raw}(i,j,n)$ and the second corrective image $gain_{unwarped}(i,j,n)$, as discussed above, are applied to the three-dimensional scan of the patient. This is discussed in detail with reference to FIG. 4. The resulting image corrected by means of the double-stage gain correction is made available by the artifact reduction means 20 to a suitable visualization means, for example to a computer monitor 30 for inspection purposes. An example of a resulting reconstructed image I3 is shown in FIG. 5. It is seen that when compared to the images shown in FIGS. 2a and 2b the ring-shaped artifact is substantially removed due to the double stage gain calibration according to the invention.

The artifact reduction means 20 according to the invention preferably comprises a first stage correction means 21 arranged to eliminate the structured noise of the output screen using the first corrective image. Preferably, the first corrective image 21a is pre-calculated and is stored in a suitable memory unit of a computer (not shown). A raw image of the patient is first processed with the first corrective image 21a. The thus obtained gain-corrected image is forwarded to an image deformation correction means 23, where a suitable unwarping function 23a is being pre-stored. The resulting gain-corrected unwarped images are then made available to the second stage gain correction means 25, where a second corrective image 25a is applied to the images resulting in a final set of images with a substantially reduced ring-shaped artifact. The final set of images is made available to the image reconstruction means 26 arranged for further processing of the final set of images, the result thereof being, for example, visualized on a computer monitor 30 for inspection purposes.

Figure 4:
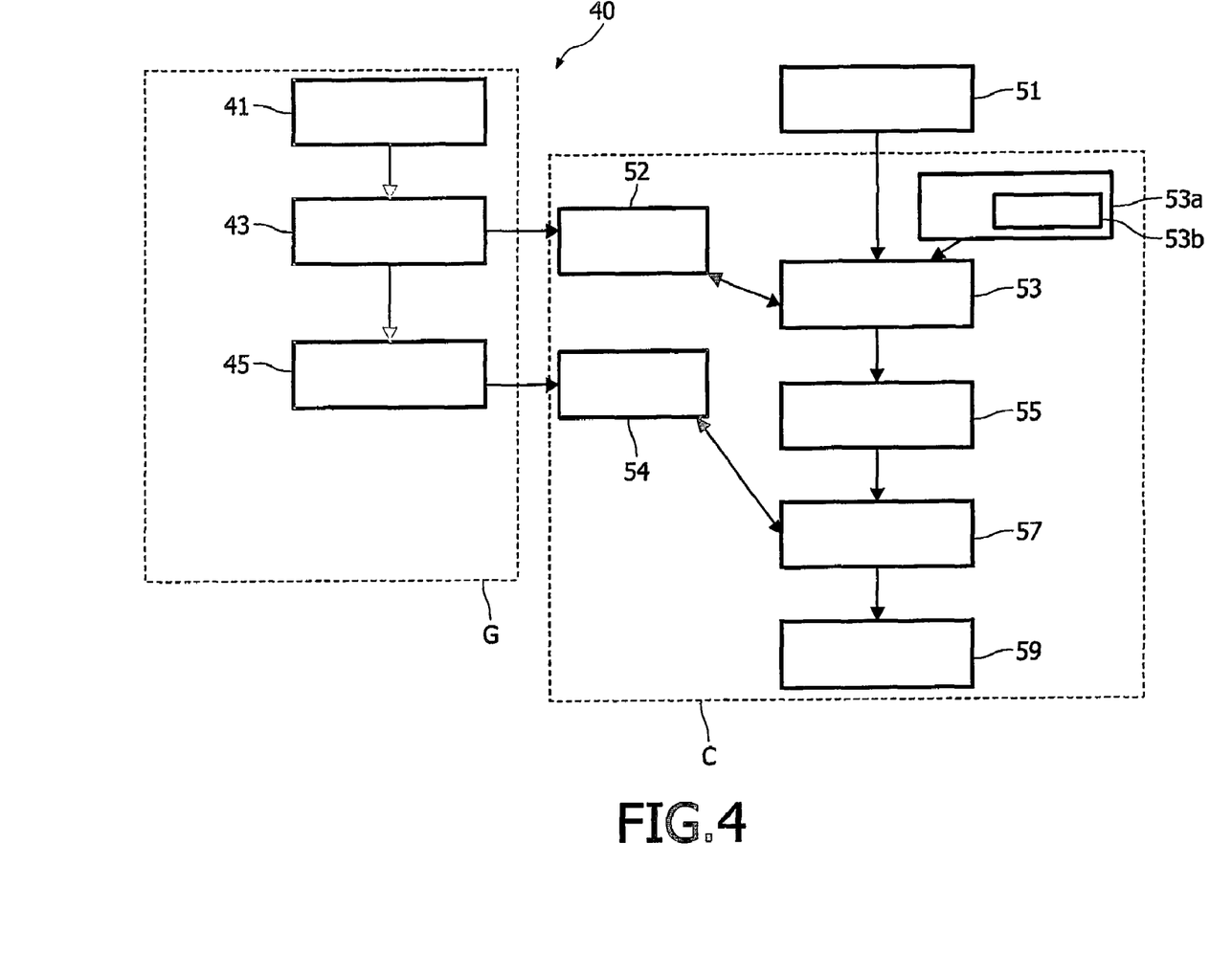
FIG. 4 shows schematically a flowchart of a computer program according to the invention.
Figure 5:
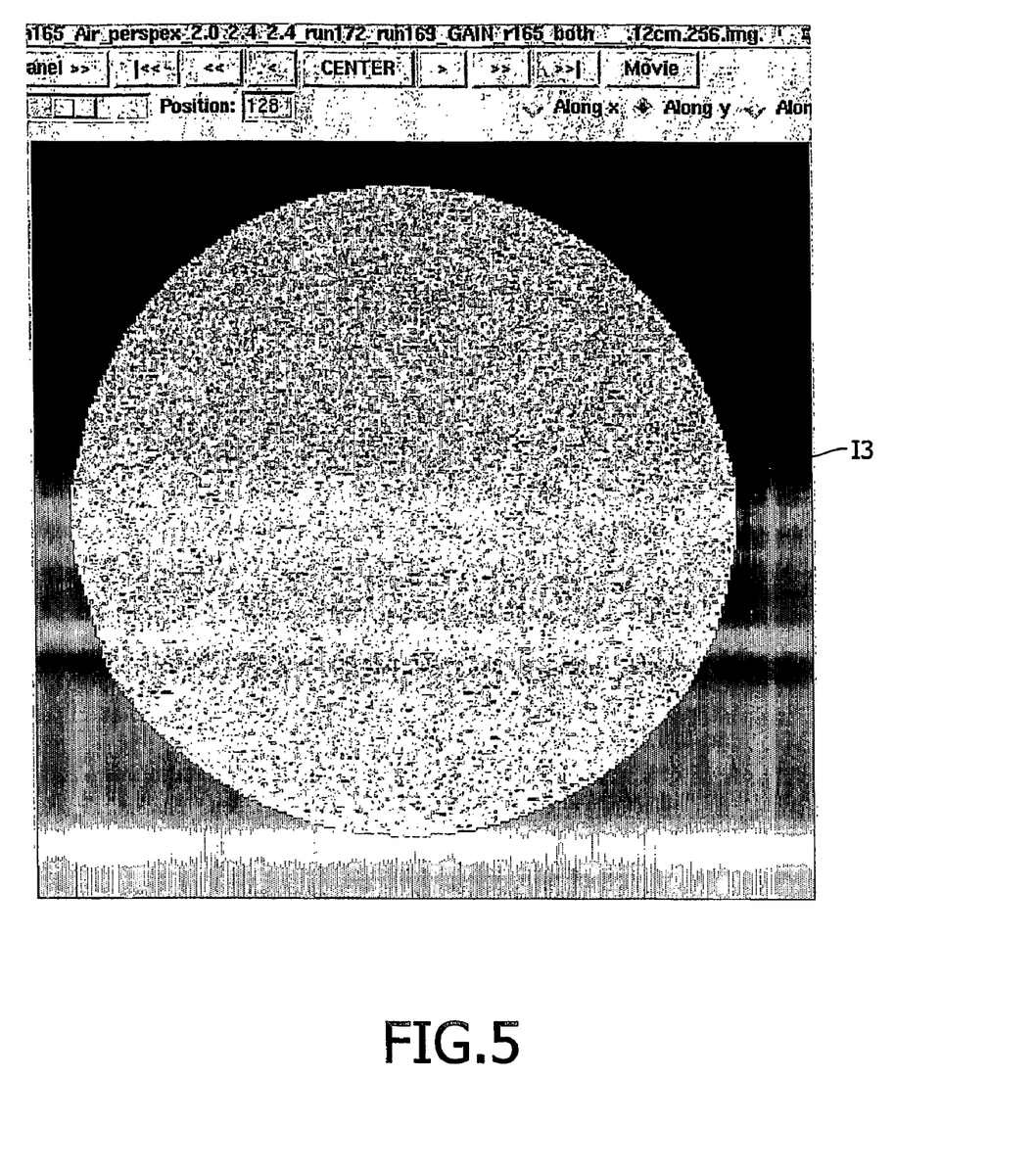
FIG. 5 shows a resulting image in a slice perpendicular to the rotational axis of the X-ray system of FIG. 3 post double-stage gain correction, according to the invention.

FIG. 4 shows schematically a flowchart 40 of an operation of the computer program according to the invention. Prior to the double-stage calibration step C, a three-dimensional gain calibration scan 41 and a three-dimensional patient scan 51 are acquired. The three-dimensional gain calibration scan 41 is used in a preparatory step G to obtain the first corrective image $gain_{raw}(i,j)$ 43 and the second corrective image $gain_{unwarped}(i,j)$ 45, respectively, according to the procedure discussed above. Preferably, the first corrective image 43 and the second corrective image 45 are pre-stored in respective look-up tables 52, 54 and are addressed by the computer program during its execution. Thus, at step 53 the double-stage gain correction algorithm carries out a gain correction of the raw images of the patient by using the first corrective image 52, yielding the gain-corrected image of the patient according to the equation:

$$Im_{gain,raw}(i, j, n) = Im_{raw}(i, j, n) \frac{\frac{1}{N^2}\sum_{i,j} gain_{raw}(i, j)}{gain_{raw}(i, j)},$$

where $\text{Im}_{gain, raw}(i,j,n)$ is a gain-corrected image of the patient;

$\text{Im}_{raw}(i,j,n)$ is a raw image of the patient;

$gain_{raw}(i,j)$ is a first corrective function constructed for a set of raw images of a gain calibration scan.

Additionally, it is possible to correct for a drift of the projection of the output screen of the image intensifier of the imaging means by applying a drift correction 53b prestored in a look-up table 53a.

Subsequently the gain-corrected images $\text{Im}_{gain, raw}(i,j,n)$ are subjected to an unwarping operation at step 55 by means of a suitable known per se in the art unwarping function 23a stored in an image deformation correction means 23 (see FIG. 3), yielding unwarped gain-corrected images of the calibration object $\text{Im}_{gain, unwraped}(i,j,n)$. At this stage the structured noise of the output screen of the image intensifier is substantially removed from the raw images of the patient, said images being also corrected for the pincushion deformation caused by external magnetic fields.

Finally, at step 57 the gain-corrected unwarped images $\text{Im}_{gain, unwarped}(i,j,n)$ are corrected with the second corrective image $gain_{unwarped}(i,j)$, preferably pre-stored in a look-up table 54, this being given by the equation:

$$Im_{gain,doublestage}(i, j, n) = Im_{gain,unwarped}(i, j, n) \frac{\frac{1}{N^2}\sum_{i,j} gain_{unwarped}(i, j)}{gain_{unwarped}(i, j)},$$

where $\text{Im}_{gain, doublestage}(i,j,n)$ is a double-stage gain corrected image of the patient;

$\text{Im}_{gain, unwarped}(i,j,n)$ is an unwarped gain corrected image of the patient;

$gain_{unwarped}(i,j)$ is the second corrective image constructed for a set of unwarped gain-corrected imaged of a gain calibration scan.

The resulting image is made available by the computer program for the further processing at step 59, preferably it is stored in a suitable memory unit of a computer.

The invention claimed is:

1. An imaging system arranged to reduce an artifact in a three-dimensional reconstructed volume comprising a plurality of planar images, said imaging system comprising:
   an image artifact reducer arranged to process said planar image with a first corrective image for eliminating a first source of structured noise in said image, thereby producing a gain corrected image, arranged to apply an unwarping function to the gain corrected image, thereby producing an unwarped gain corrected image, and arranged to apply a second corrective image to the unwarped gain corrected image for eliminating a second source of structured noise in said image and thereby reduce artifacts in the three-dimensional reconstructed volume.

2. The imaging system according to claim 1, wherein
   the first corrective image comprises a first gain correction data; and
   the second corrective image comprises a second gain correction data.

3. The imaging system according to claim 2, wherein:
   the first gain correction data comprises a result of an averaging of a plurality of raw images of a gain calibration scan; and
   the second gain correction data comprises a result of an averaging of a plurality of raw images of the gain calibration scan after the plurality of raw images of the gain calibration scan is processed utilizing the first corrective image after the unwarping function is applied to the processed first corrective image.

4. The imaging system according to claim 1, the image being acquired by an image intensifier, wherein the first source of noise comprises a noise of an output screen of the image intensifier and the second source of noise comprises a noise of an input screen of the image intensifier.

5. The imaging system according to claim 4, wherein the first corrective image comprises a drift correction data arranged to correct for a movement of a projection of the output screen of the image intensifier during a rotational scan.

6. The imaging system according to claim 1, wherein the imaging system is an X-ray examination apparatus.

7. A method for reducing an artifact in a three-dimensional reconstructed volume comprising a plurality of planar images, said method comprising the steps of:
   processing the image using a first corrective image to eliminate a first source of structured noise in the image yielding a first-stage corrected image;
   processing the first-stage corrected image with an unwarping function yielding an unwarped first-stage corrected image; and
   processing the unwarped first-stage corrected image with a second corrective image to eliminate a second source of structured noise in the image yielding a second-stage corrected image and thereby reduce artifacts in the three-dimensional reconstructed volume.

8. A method according to claim 7, wherein
   the first corrective image comprises a first gain correction data, said first corrective image being constructed for a raw image of a gain calibration scan;
   the second corrective image comprises a second gain correction data, said second corrective image being constructed from the raw image of the gain calibration scan after the raw image of the gain calibration scan is processed by the first corrective image and after the unwarping function is applied to the processed first corrective image.

9. A method according to claim 8, wherein:
   the first gain correction data comprises a result of an averaging of a plurality of raw images of the gain calibration scan;
   the second gain correction data comprises a result of an averaging of a plurality of raw images of the calibration object after the raw image of the gain calibration scan is processed by the first corrective image and after the unwarping function is applied to the processed first corrective image.

10. A computer program stored on a computer readable memory medium, the computer program being arranged to reduce an artifact in a three-dimensional reconstructed volume comprising a plurality of planar images by processing the planar image with a first corrective image to eliminate a first source of structured noise in the image, thereby producing a gain corrected image, by applying an unwarping function to the gain corrected image, thereby producing an unwarped gain corrected image, and applying a second corrective image to the unwarped gain corrected image to eliminate a second source of structured noise in the image and thereby reduce artifacts in the three-dimensional reconstructed volume.

* * * * *